(12) United States Patent
Harty et al.

(10) Patent No.: US 11,291,189 B2
(45) Date of Patent: *Apr. 5, 2022

(54) METHOD FOR COMMUNICATING WITH AN ELECTRONIC DEVICE AND AN ELECTRONIC DEVICE LOCATABLE ON OR IN AN ANIMAL

(71) Applicant: DAIRYMASTER, Causeway (IE)

(72) Inventors: Edmond Patrick Harty, Ballyheigue (IE); Liam Eoghan Mullane, Newcastlewest (IE); John Gerard Daly, Tralee (IE)

(73) Assignee: DAIRYMASTER, County Kerry (IE)

( * ) Notice: Subject to any disclaimer, the term of this patent is extended or adjusted under 35 U.S.C. 154(b) by 0 days.

This patent is subject to a terminal disclaimer.

(21) Appl. No.: 15/960,003

(22) Filed: Apr. 23, 2018

(65) Prior Publication Data

US 2018/0235184 A1 Aug. 23, 2018

Related U.S. Application Data

(62) Division of application No. 14/897,421, filed as application No. PCT/IE2014/000011 on Jun. 16, 2014, now Pat. No. 9,974,284.

(30) Foreign Application Priority Data

Jun. 14, 2013 (IE) .................................... 2013/0193
Jun. 14, 2013 (IE) .................................... 2013/0194

(51) Int. Cl.
*A01K 29/00* (2006.01)
*A01K 11/00* (2006.01)
(Continued)

(52) U.S. Cl.
CPC .......... *A01K 29/005* (2013.01); *A01K 11/006* (2013.01); *A61B 5/0022* (2013.01);
(Continued)

(58) Field of Classification Search
CPC ................ A01K 11/006; A01K 29/005; A61B 2503/40; A61B 2562/0219; A61B 5/0022;
(Continued)

(56) References Cited

U.S. PATENT DOCUMENTS 7,026,941 B1 4/2006 Anderson
9,298,756 B1 * 3/2016 Johnson .............. G06F 16/9554
(Continued)

FOREIGN PATENT DOCUMENTS

EP 2 000 023 A1 12/2008
WO 2007/132245 A1 11/2007

OTHER PUBLICATIONS

International Search Report for PCT/IE2014/000011 dated Sep. 3, 2014.

*Primary Examiner* — Ojiako K Nwugo
(74) *Attorney, Agent, or Firm* — Sughrue Mion, PLLC

(57) ABSTRACT

An electronic monitoring device for attaching to an animal includes an NFC module facilitating wireless communication between a smart phone and the monitoring device, an accelerometer for monitoring acceleration of the head of the animal, and a microprocessor which determines various states of the animal from signals received from the accelerometer. The smart phone is programmed by a software application which allows an identifying code of the monitoring device to be read from the memory chip and cross-referenced in the smart phone with the identity of an animal, which can be inputted into the smart phone. Data relating to the states(s) of the animal can be read from the microprocessor through the NFC module into the smart phone. Additionally, data relating to the animal stored in a cloud server corresponding to the state or states of the animal is downloaded from the cloud server by the smart phone.

20 Claims, 4 Drawing Sheets

(51) Int. Cl.
  *A61B 5/00* (2006.01)
  *A61B 5/11* (2006.01)
(52) U.S. Cl.
  CPC ........... *A61B 5/1114* (2013.01); *A61B 5/1118* (2013.01); *A61B 5/1121* (2013.01); *A61B 5/1123* (2013.01); *A61B 5/7246* (2013.01); *A61B 5/7278* (2013.01); *A61B 5/7282* (2013.01); *A61B 2503/40* (2013.01); *A61B 2562/0219* (2013.01)
(58) Field of Classification Search
  CPC ... A61B 5/1114; A61B 5/1118; A61B 5/1121; A61B 5/1123; A61B 5/7246; A61B 5/7278; A61B 5/7282; A61D 17/002
  USPC .................. 340/573.1, 573.3; 119/51.2, 174
  See application file for complete search history.

(56) References Cited

U.S. PATENT DOCUMENTS

| | | | | |
|---|---|---|---|---|
| 2005/0139665 A1* | 6/2005 | Sato | ..................... | G06Q 10/087 235/385 |
| 2007/0288249 A1* | 12/2007 | Rowe | ................... | A01K 1/0023 705/7.11 |
| 2008/0129457 A1* | 6/2008 | Ritter | ..................... | G07C 9/257 340/10.1 |
| 2008/0266107 A1 | 10/2008 | Rodgers | | |
| 2009/0051490 A1* | 2/2009 | Childress | ............... | G06K 17/00 340/5.92 |
| 2009/0189769 A1* | 7/2009 | Schaffler | ................ | H01Q 7/005 340/572.7 |
| 2010/0134257 A1 | 6/2010 | Puleston et al. | | |
| 2012/0224076 A1* | 9/2012 | Niedermeyer | ......... | G06K 17/00 348/211.2 |
| 2013/0176115 A1* | 7/2013 | Puleston | ............... | H01Q 1/2225 340/10.51 |
| 2013/0194097 A1* | 8/2013 | Joseph | ............... | G08B 13/2417 340/572.1 |
| 2013/0255593 A1* | 10/2013 | Hilarides | ............... | A01K 11/004 119/840 |
| 2013/0260679 A1* | 10/2013 | Su | ............................ | H04B 5/02 455/41.1 |
| 2013/0275316 A1* | 10/2013 | Teng | .................... | G06Q 30/018 705/317 |
| 2013/0296669 A1* | 11/2013 | Chen | .................... | A61B 5/6816 600/324 |
| 2014/0302783 A1* | 10/2014 | Aiuto | ................... | H04B 5/0031 455/41.2 |
| 2018/0235184 A1* | 8/2018 | Harty | ................... | A61B 5/1123 |

* cited by examiner

METHOD FOR COMMUNICATING WITH AN ELECTRONIC DEVICE AND AN ELECTRONIC DEVICE LOCATABLE ON OR IN AN ANIMAL

CROSS REFERENCE TO RELATED APPLICATIONS

This application is a divisional of U.S. patent application Ser. No. 14/897,421 filed Dec. 10, 2015, which is a National Stage Application of PCT/IE2014/000011 filed Jun. 16, 2014, which claims priority from Irish Patent Application S2013/0193 filed Jun. 14, 2013 and Irish Patent Application No. S2013/0194 filed Jun. 14, 2013, the disclosures of which are incorporated herein in their entirety by reference.

BACKGROUND OF THE INVENTION

The present invention relates to a method for communicating with an electronic device, and in particular, with an electronic memory of an electronic device which is locatable externally on or internally in an animal. The invention also relates to an electronic device locatable externally on or internally in an animal which is configurable to communicate with an external powered device.

Electronic devices for monitoring various characteristics of an animal in order to detect one or more of a plurality of states of an animal are known. Such electronic devices monitor movement of an animal, or movement of a part of an animal, for example, the head of an animal. Additionally, or alternatively, such electronic devices monitor the body temperature, heart rate, blood pressure and/or other characteristics of an animal. By knowing the movement of an animal, the temperature of the animal, the heart rate and other such characteristics of an animal over an extended period of time, one or more of a plurality of states of the animal can be detected, such states may, for example, be a state of oestrus, feeding, ruminating, resting and the like. In such electronic devices the characteristics are monitored either continuously or periodically, and the data indicative of the monitored characteristics of the animal is stored in memory in such electronic devices. The electronic devices may be programmed so that at predefined intervals stored data indicative of the characteristics of an animal are transmitted by the electronic device for reception by a base station, which analyses the stored data in order to detect one or more states of the animal. The data transmitted for reception by the base station, in general, is the data which has been monitored and stored since the last data transmission. In order to transfer such data, the electronic device is provided with either a transmitter or a transceiver. If only a transmitter is provided, transmissions are generally carried out at the end of predefined time intervals. However, if the electronic device is provided with a transceiver, the stored data may be transmitted at programmable predefined time periods and/or in response to a signal received by the electronic device from the base station. In general, such transmissions are carried out by radio wave transmissions over a relatively long distance. Alternatively, the electronic devices may be configured to communicate with a telecommunications network, for example, a mobile phone network, and the data is transmitted to the base station as an SMS message. In general, an identifying code which identifies the electronic device is stored in memory in the electronic device, and as each data transmission of data is being made, the identifying code of the electronic device is transmitted with the data. The base station typically stores the identifying code of a plurality of identifying devices cross-referenced with the identity of the animal to which the electronic device is attached.

Such electronic devices may be of the type referred to as an ear tag which is suitable for attaching to the ear of an animal, or such electronic devices may be of the type which are attached to the animal by a strap or other suitable ligature extending around a part of the animal, for example, the neck of the animal, the leg of an animal, the tail or the like of the animal. Such electronic devices are of great benefit to a farmer, since by monitoring and detecting various states of an animal, in the event of a state requiring intervention by the farmer, such intervention can be readily and timely made. However, a disadvantage of such devices is that data relating to the state of the animal and the identifying code of the device, typically is only available from the base station, which in many cases, if the base station is not located on the farm of a farmer, which in many cases it is not, accessing the data stored in the device by the farmer can be inconvenient and slow.

There is therefore a need for a method for communicating with an electronic device located externally on or internally in an animal, and in particular, there is a need for a method for communicating with an electronic memory of such an electronic device which overcomes problems of known methods and devices. There is also a need for an electronic device locatable externally on or internally in an animal which can readily easily be communicated with.

SUMMARY OF THE INVENTION

The present invention is directed towards providing such a method and such an electronic device.

According to the invention there is provided a method for communicating with an electronic memory of an electronic device locatable externally on or internally in an animal, the method comprising locating a low energy communications module on the device configured to wirelessly communicate an external powered device with the electronic memory.

In one aspect of the invention an external powered device configured to wirelessly communicate with the low energy communications module is brought into close proximity with the electronic device, and wireless communication is initiated between the external powered device and the electronic device.

Preferably, wireless communication is initiated between the external powered device and the electronic module by the external powered device.

Advantageously, data is read wirelessly from the electronic memory of the electronic device by the external powered device through the low energy communications module. Ideally, an identifying code identifying the electronic device is read wirelessly from the electronic memory of the electronic device by the external powered device through the low energy communications module.

In one aspect of the invention data is written wirelessly to the electronic memory of the electronic device by the external powered device through the low energy communications module.

In another aspect of the invention an identifying code of an animal on which the electronic device is located is written wirelessly to the electronic memory of the electronic device by the external powered device through the low energy communications module.

In one embodiment of the invention the electronic device is configured to monitor at least one of a plurality of states of the animal and to store data indicative of the monitored states, and the stored data indicative of the monitored states of the animal is downloaded wirelessly from the electronic device to the external powered device by the external powered device through the low energy communications module.

In one aspect of the invention the downloaded data indicative of the monitored states of the animal is stored in the external powered device.

In another aspect of the invention the identifying code identifying the animal is one of entered into the external powered device or downloaded wirelessly from the electronic memory of the electronic device by the external powered device through the low energy communications module. Preferably, the identifying code of the animal is downloaded wirelessly through the low energy communications module from the electronic memory of the electronic device to the external powered device along with the downloaded data indicative of the states of the animal. Advantageously, the downloaded stored data indicative of the state of the animal is stored in the external powered device cross-referenced with the identifying code of the animal.

In another aspect of the invention the identifying code identifying the electronic device is wirelessly downloaded through the low energy communications module from the electronic memory of the electronic device to the external powered device along with the stored data indicative of the states of the animal.

Preferably, the identifying code identifying the electronic device and the identifying code identifying the animal are stored and cross-referenced with each other in the external powered device.

In one embodiment of the invention the electronic device comprises a signal processor configured to be resettable wirelessly by an external powered device through the low energy communications module.

In another embodiment of the invention the signal processor of the electronic device is configured to be programmable wirelessly by an external powered device through the low energy communications module.

In another embodiment of the invention the signal processor of the electronic device is configured to communicate with an external powered device through the low energy communications module.

In a further embodiment of the invention the signal processor of the electronic device is configured for the downloading of data therefrom to an external powered device.

In a still further embodiment of the invention the signal processor of the electronic device is configured for uploading of data thereto from an external powered device.

Preferably, communications between an external powered device and the signal processor of the electronic device is controlled by the external powered device.

In another embodiment of the invention the external powered device is programmed to control communications between itself and the signal processor of the electronic device.

Preferably, the low energy communications module is configured to be electrically powered wirelessly by an external powered device.

Advantageously, the low energy communications module is configured to be electrically powered wirelessly by induction by an external powered device.

Ideally, the low energy communications module is configured to be electrically powered wirelessly by electromagnetic induction by an external powered device.

Preferably, the low energy communications module is configured to be wirelessly electrically powered by a wireless data communications signal from an external powered device.

In one embodiment of the invention the low energy communications module is electrically powered wirelessly through an induction coil located in the electronic device.

Preferably, the induction coil is configured as a loop antenna for wirelessly communicating the low energy communications module with an external powered device.

In another aspect of the invention the external powered device is programmed to wirelessly communicate with the low energy communications module in the electronic device.

In a further embodiment of the invention the external powered device is configured to communicate wirelessly with a telecommunications network.

Preferably, the external powered device is configured to communicate with a remote computer.

Advantageously, data downloaded from the electronic device is uploaded to the remote computer by the external powered device.

Preferably, the external powered device downloads data relating to an animal on which the electronic device is located from the remote computer.

Advantageously, the data downloaded by the external powered device from the remote computer relating to an animal on which the electronic device is located is uploaded wirelessly by the external powered device to the electronic device through the low energy communications module.

In one embodiment of the invention the remote computer comprises a cloud computer server.

Preferably, the external powered device comprises a programmable smart mobile device.

Advantageously, the smart mobile device is programmed by a software application (app) for communicating wirelessly with the electronic device through the low energy communications module.

Preferably, the smart mobile device is programmed by the app to display on a visual display screen thereof data downloaded from the electronic device.

In one aspect of the invention the smart mobile device is programmed by the app to display data relating to an animal on which the electronic device is located downloaded from the remote computer in response to the smart mobile device downloading one of the identifying code of the electronic device and the identifying code of the animal from the electronic device.

In one embodiment of the invention the low energy communications module comprises a blue tooth low energy module.

In an alternative embodiment of the invention the low energy communications module comprises a Near Field Communications (NFC) module. Preferably, communications between the NFC module and an external powered device is in an NFC protocol.

Advantageously, the external powered device is programmed to wirelessly communicate with the low energy communications module in the electronic device.

Preferably, the smart mobile device is programmed by the app to communicate wirelessly with the electronic device through the NFC module in an NFC protocol.

In another embodiment of the invention the external power device comprises a smart mobile phone.

The invention also provides an electronic device configured for locating externally on or internally in an animal comprising an electronic memory and a low energy communications module configured to wirelessly communicate an external powered device with the electronic memory.

In one aspect of the invention the low energy communications module is configured to wirelessly communicate an external powered device with the electronic memory of the electronic device for reading data from the electronic memory to the external powered device.

In another aspect of the invention the low energy communications module is configured to wirelessly communicate an external powered device with the electronic memory of the electronic device for writing data to the electronic memory by the external powered device.

Preferably, the electronic device comprises a signal processor, and the low energy communications module is configured to wirelessly communicate an external powered device with the signal processor.

Advantageously, the signal processor is resettable, and the low energy communications module is configured to reset the signal processor in response to a reset signal wirelessly received from an external powered device.

Advantageously, the signal processor is programmable wirelessly by an external powered device through the low energy communications module. Preferably, the signal processor of the electronic device is configured to communicate with an external powered device through the low energy communications module.

In another aspect of the invention the electronic device comprises a monitoring means for monitoring a state of an animal on which the electronic device is located, and the signal processor is configured for processing signals read from the monitoring means, and for producing data indicative of a state of the animal.

In a further aspect of the invention the signal processor is configured to store the data indicative of the state of the animal, and the low energy communications module is configured for wirelessly communicating an external powered device with the signal processor for downloading the stored data indicative of the state of the animal to the external powered device.

In one embodiment of the invention the low energy communications module is configured for wirelessly communicating an external powered device with the signal processor for downloading the stored data indicative of the state of the animal to the external powered device cross-referenced with an identifying code indicative of the identity of the electronic device stored in the electronic memory of the electronic device.

In another embodiment of the invention the electronic device comprises an induction coil configured to provide electrical power to the low energy communications module in response to an electromagnetic field from an external powered device. Preferably, the induction coil is configured as a loop antenna for wirelessly communicating an external powered device with the low energy communications module.

Preferably, the low energy communications module is electrically coupled to a printed circuit board, and the induction coil is formed by an electrically conductive track on the printed circuit board. Advantageously, the induction coil extends around the printed circuit board adjacent the periphery thereof.

In another embodiment of the invention the electronic device comprises a long range wireless communicating means for communicating the electronic device with a remote computing means. Preferably, the long range wireless communicating means comprises a radio wave transmitter. Advantageously, the long range wireless communicating means comprises a radio wave transceiver.

In one embodiment of the invention the low energy communications module comprises a blue tooth low energy module.

In an alternative embodiment of the invention the low energy communications module comprises an NFC module.

Preferably, the NFC module is configured for communication with an external powered device when the external powered device is not more than 100 mm from the NFC module. Advantageously, the NFC module is configured for communicating with an external powered device when the external powered device is not more than 75 mm from the NFC module.

Ideally, the NFC module is configured for communicating with an external powered device when the external powered device is not more than 50 mm from the NFC module.

Additionally, the invention provides a smart mobile device programmed by an app to communicate with the electronic device according to the invention.

Preferably, the smart mobile device is programmed by the app to communicate with the electronic device in an NFC protocol.

Further the invention provides in combination an electronic device according to the invention, and an external powered device configured to communicate with the electronic device through the low energy communications module.

Preferably, the external powered device comprises the smart mobile device according to the invention.

In another embodiment of the invention the combination according to the invention further comprises a remote computer, and a communicating means for communicating between the electronic device and the remote computer.

Preferably, the communicating means comprises a relay station comprising a radio transceiver for communicating with the electronic device, and a GSM module configured to communicate with the remote computer.

Advantageously, the remote computer comprises a cloud computer server.

The advantages of the invention are many. A particularly important advantage of the invention is that by virtue of the fact that the electronic device is provided with a low energy communications module, such as an NFC module which is configured to wirelessly communicate with an external powered device, a farmer can readily easily communicate and download data stored in the electronic memory of the electronic device directly into an external powered device, for example, a smart mobile device, such as a smart mobile phone suitably programmed with a suitable software application. Additionally, the smart mobile device may be programmed to analyse the data downloaded from the electronic device in order to assess the status of the animal. Furthermore, the provision of the low energy communications module such as an NFC module in the electronic device permits downloading of an identifying code of the electronic device which is stored in electronic memory of the electronic device and cross-referencing the identifying code of the electronic device with an identifying code of the animal. This, thus, permits the identity of an animal to be readily identified by communicating with the electronic device through the NFC module by an external powered device, for example, a smart mobile phone by merely bringing the smart mobile phone into close proximity, typically, within 50 mm of the electronic device in order to read out the identifying code of the electronic device and then identifying the cow from the cross-referenced data in the mobile phone.

A further advantage of the method and the electronic device according to the invention is that the provision of the low energy communications module, such as an NFC module in the electronic device where the electronic device comprises a signal processor, for example, a microprocessor, the signal processor can be programmed by the external powered device, and furthermore, can be reset by the external powered device. A further advantage of the invention is that by virtue of the fact that the NFC module is powered by the external powered device during communications through the NFC module, no additional power is required from an on-board power supply, for example, a battery of the electronic device to power the NFC module during communication with the electronic device through the NFC module.

BRIEF DESCRIPTION OF THE DRAWINGS

The invention will be more clearly understood from the following description of some preferred embodiments thereof, which are given by way of example only, with reference to the accompanying drawings, in which.

DETAILED DESCRIPTION OF THE INVENTION

Figure 1:
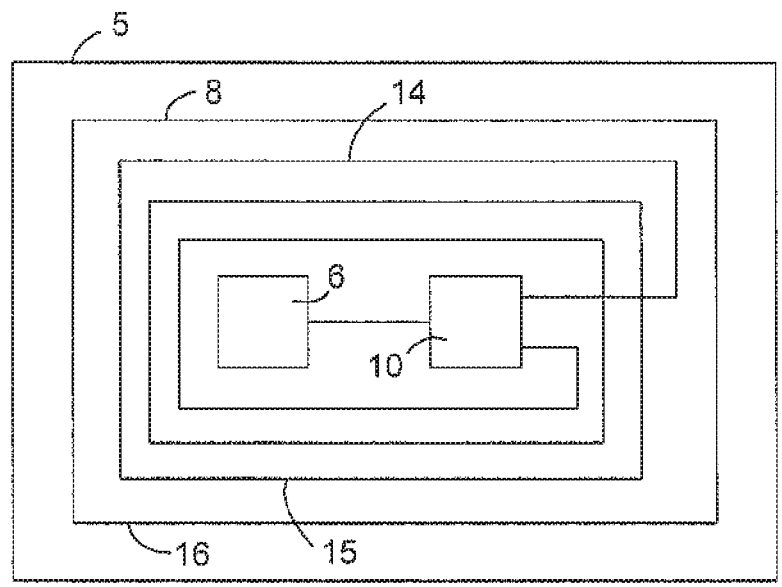
FIG. 1 is a block representation of an electronic device according to the invention which is locatable on an animal for identifying the animal.
Figure 2:
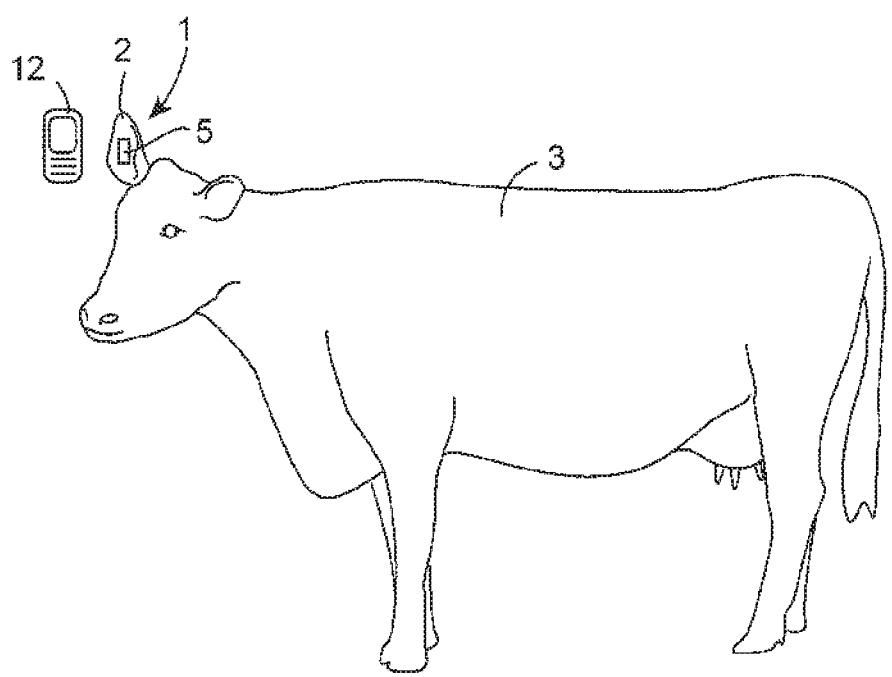
FIG. 2 is a perspective view of an animal with the electronic device of FIG. 1 attached thereto.
Figure 3:
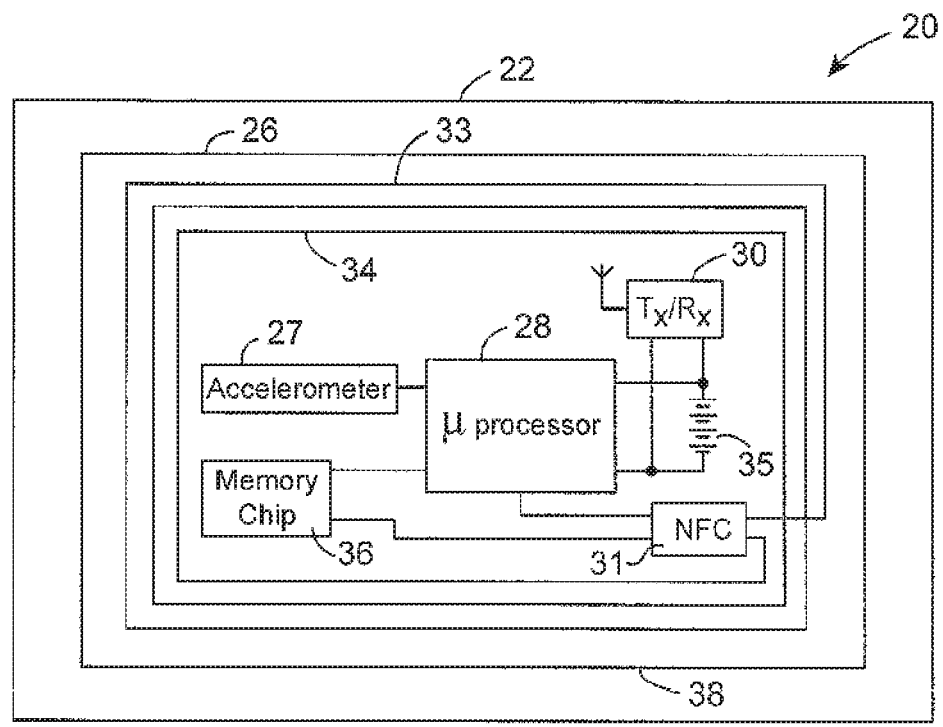
FIG. 3 is a block representation of an electronic device according to another embodiment of the invention for locating on an animal for monitoring a characteristic or a state of the animal.
Figure 4:
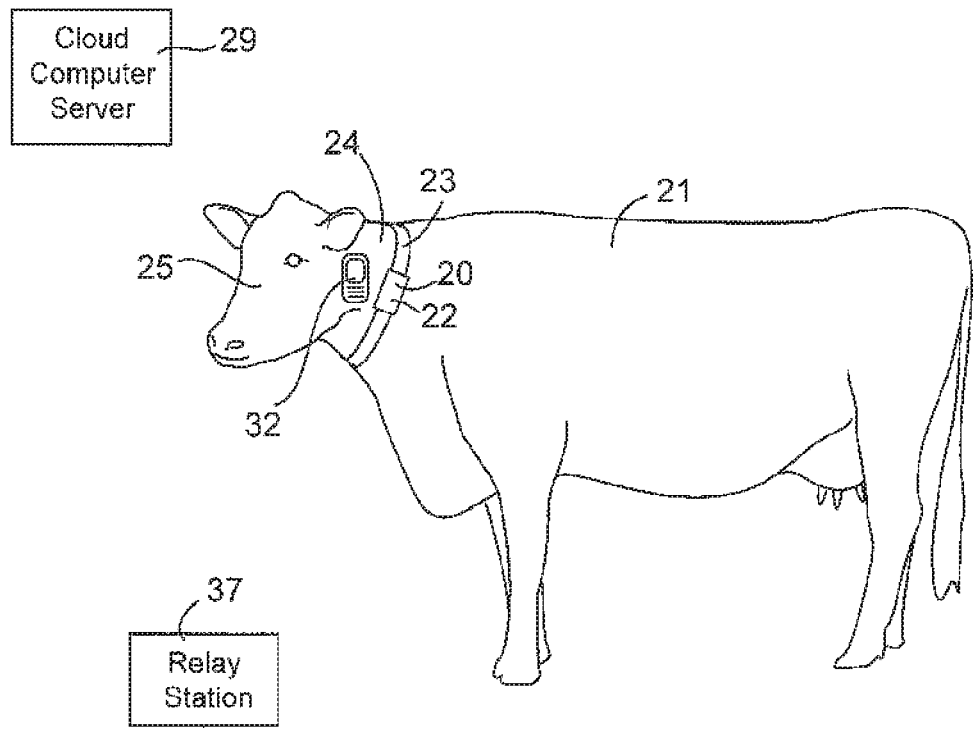
FIG. 4 is a perspective view of an animal with the electronic device of FIG. 3 attached thereto.

Referring to the drawings and initially to FIGS. 1 and 2, there is illustrated an electronic device according to the invention, which in this case is provided as an ear tag, indicated generally by the reference numeral 1, for attaching to an ear 2 of an animal 3, for example, the ear 2 of a cow. The ear tag 1 is a tag-like device, and comprises a tag-like housing 5. A stud (not shown) is provided for securing the ear tag 1 to the ear 2 of the animal 3. Such studs for securing an ear tag to an ear of an animal will be well known to those skilled in the art. In this embodiment of the invention the ear tag 1 is configured as an identity tag for identifying the animal, and comprises a storing means which comprises an electronic memory, namely, an electronic memory chip 6 which is mounted on a printed circuit board (PCB) 8, both of which are housed in the housing 5. An identifying code for identifying the ear tag 1 is stored in the memory chip 6, and the identifying code is unique and specific to the ear tag 1.

A low energy communications module, which in this embodiment of the invention comprises a Near Field Communications (NFC) module 10 which is also located within the housing 5. The NFC module 10 is mounted on the PCB 8 and is configured to wirelessly transmit the identifying code stored in the memory chip 6 in an NFC protocol to an external powered device, in this case a smart mobile phone 12 in response to a wake-up signal transmitted by the smart phone 12 in an NFC protocol when the smart phone 12 is in close proximity with the ear tag 1, in this case, when the ear tag 1 and the smart phone 12 are within a distance of less than 50 mm of each other. The NFC module is configured to communicate in the NFC protocol at a frequency of the order of 13.56 MHz.

The smart phone 12 or other smart mobile device is programmed by a software application, namely, an app which configures the smart phone 12 to communicate with the ear tag 1 in the NFC protocol, and when programmed by the app, the smart mobile device is also according to the invention. Furthermore, the combination of the electronic device 1 and the smart mobile device when programmed by the app is also according to the invention. The app of the smart phone 12 also configures the smart phone 12 to receive the identifying code of the ear tag 1 transmitted through the NFC module 10. Furthermore, the app of the smart phone 12 also permits inputting of the identity of the animal 3 to which the ear tag 1 is attached into the smart phone 12, and cross-referencing the identity of the animal 3 with the identifying code of the ear tag 1 in the smart phone 12. The identity of the animal may be inputted and stored in the smart phone 12 as any suitable numeric or alphanumeric code, and typically, is inputted and stored in the smart phone 12 as an identifying code assigned by a State agency to identify the animal or an identifying code generated by a farmer to identify the animal, or both such identifying codes. Additionally, the app with which the smart phone 12 is programmed configures the smart phone 12 to store data relating to various states, conditions, characteristics and the like of the animal 3, which may be downloaded from a cloud computer server, and which are then cross-referenced in the smart phone 12 with the identifying code of the animal, which in turn is cross-referenced in the smart phone 12 with the identifying code of the ear tag 1.

An induction coil 14 is formed by an electrically conductive track 15 which is formed during the formation of the PCB 8 and extends around the PCB 8 adjacent the periphery 16 thereof. The induction coil 14 is configured to form a loop antenna through which data signals are wirelessly communicated between the NFC module 10 and the smart phone 12 during NFC communication therebetween. The induction coil 14 is also configured for powering the NFC module 10 by the smart phone 12 when the smart phone 12 is in close proximity to the ear tag 1 during communication through the NFC module 10 for reading the identifying code of the ear tag 1 from the memory chip 6. The induction coil 14 is electrically connected to the NFC module 10, and is configured so that when subjected to the varying electromagnetic field produced by the data communications signal from the smart phone 12 during NFC communication between the smart phone 12 and the NFC module 10, a current is induced in the induction coil 14 for powering the NFC module 10 during communication with the smart phone 12.

In use, when the ear tag 1 is initially attached to an ear 2 of an animal 3, the smart phone 12 with the app installed therein and activated is brought into close proximity with the ear tag 1, in other words, the smart phone 12 is brought within 50 mm of the ear tag 1. The smart phone 12 is then activated to wirelessly transmit a wake-up signal to the ear tag 1 in the NFC protocol. The electromagnetic field resulting from the data communications signal from the smart phone 12 powers the NFC module during communication between the smart phone 12 and the NFC module 10. On reception of the wake-up signal, the NFC module 10 wirelessly transmits the identifying code of the ear tag 1 in the NFC protocol for reception by the smart phone 12. On receipt of the identifying code of the ear tag 1, the identifying code of the animal is inputted into the smart phone 12 which is still operating under the control of the app, and the identifying code of the ear tag 1 and the identifying code from the animal 2 are stored in the smart phone 12 and cross-referenced with each other as the smart phone 12 continues to operate under the control of the app.

If data relating to particulars of the animal 3, for example, health conditions and characteristics of the animal, are already stored in the smart phone 12, the particulars are also cross-referenced with the stored identifying codes of the ear tag 1 and the animal 3.

It is envisaged that in a herd of animals, for example, a herd of cows, each animal will have one ear tag 1 attached to one of its ears 2. The respective ear tags 1 which will be attached to the ears of the animals will be provided, typically at manufacture of the ear tags 1, with respective unique identifying codes, unique to the respective specific ear tags 1. The identifying codes will be written to and stored in the memory chips 6 at manufacture. As the ear tags 1 are being attached to the ears 2 of the respective animals 3, the identifying codes will be read from the memory chips 6 of the corresponding ear tags 1 through the NFC modules 10 by the smart phone 12 operating under the control of the app. As the identifying code is read from the memory chip 6 of each ear tag 1, the identifying code of the animal to which that ear tag is attached if it has not already been stored in the smart phone 12 will be inputted into the smart phone 12, and then cross-referenced in the smart phone 12 with the identifying code read from the memory chip 6 of the corresponding ear tag 1.

When it is subsequently desired to identify one of the animals of the herd of animals, the smart phone 12 is brought into close proximity within 50 mm of the ear tag 1 of the corresponding animal 3, and the identifying code of the ear tag 1 is read by the smart phone 12 under the control of the app from the memory chip 6 of the corresponding ear tag 1 through the NFC module 10. The smart phone 12 under the control of the app then searches the identifying codes of the respective ear tags 1 stored therein, and on finding the identifying code of the corresponding ear tag 1, the smart phone 12 then displays the identifying code of the animal. Additionally, if various conditions, characteristics or states of the animals are stored in the smart phone 12, data indicative of the conditions, characteristics or states of the animal is then displayed on the visual display screen of the smart phone 12. If data indicative of the conditions, characteristics and states of the animal is not already stored in the smart phone 12, and is available, for example, from a base station or a cloud computer server, where such data may be stored, the data indicative of the condition, characteristic and/or state of that animal is downloaded to the smart phone 12 and displayed on the visual display screen of the smart phone 12.

Referring now to FIGS. 3 to 6, there is illustrated an electronic device according to another embodiment of the invention which in this case is an electronic monitoring device, indicated generally by the reference numeral 20, for monitoring various states of an animal 21, for example, a cow. The states of the animal 21 monitored by the monitoring device 20 may, for example, be one or more of the following: the onset of oestrus, the intensity of the onset of oestrus, feeding, ruminating, resting and other such states of the animal. The monitoring device 20 may also be configured to monitor the temperature, blood pressure, heart rate and other health conditions of the animal, and it may also be configured to monitor the onset of parturition in the animal. When monitoring for the onset of oestrus, the monitoring device may be of the type sold under the Trade Mark MOOMONITOR by Dairymaster of County Kerry, Ireland. Such a monitoring device as the device sold under the Trade Mark MOOMONITOR will be well known to those skilled in the art.

The electronic monitoring device 20 comprises a housing 22 which is secured to an appropriate part of the animal 21 by a strap 23. When the electronic monitoring device 20 is of the type supplied under the Trade Mark MOOMONITOR, the housing 22 is adapted to be secured to one side of the neck 24 of the animal 21 adjacent the head 25 thereof by the strap 23, for determining whether the head 25 of the animal 21 is in a raised state or a lowered state and also for detecting the level of activity of the animal 21. A printed circuit board (PCB) 26 is located within the housing 22. An accelerometer 27 is mounted on the PCB 26 within the housing 22, and produces signals which are indicative to the acceleration to which the accelerometer 27 is subjected along two axes at right angles to each other, namely, along an X-axis and a Y-axis. The accelerometer 27 is located in the housing 22 so that when the housing 22 is secured to the neck 24 of the animal 21 by the strap 23, the signal produced by the accelerometer 27 indicative of the acceleration to which the accelerometer is subjected along one of the X and Y axes is indicative of the state of the head 25 of the animal 21, in other words, whether the head 25 of the animal 21 is in the raised state or the lowered state, and the signal produced by the accelerometer 27 indicative of the acceleration to which the accelerometer 27 is subjected along the other one of the X and Y axes is indicative of the level of activity of the animal 21.

A signal processor, which in this embodiment of the invention comprises a microprocessor 28, is mounted on the PCB 26 within the housing 22 for reading the signals from the accelerometer 27. The microprocessor 28 is configured to determine from the signals read from the accelerometer 27 the state of the head 25 of the animal 21, and the level of activity of the animal 21. From this data various states of the animal 21 can be determined as will be discussed below.

A transceiver 30 is mounted on the PCB 26 within the housing 22 for transmitting data indicative of the state of the animal 21, for reception by a remote computing means, namely, a cloud computer server 29 or for reception by one or more relay stations 37 when the animal 21 comes within range of one of the relay stations 37 for subsequent transmission by the relay station to the cloud computer server 29. Data relating to the animal would be stored on the cloud computer server 29. Alternatively, instead of storing data relating to the animal on a cloud computer server, the data may be stored on a computer at a remote base station.

In this embodiment of the invention a single relay station 37 is provided, and the data relating to the animal is stored in the cloud computer server 29. The data transmitted by the transceiver 30 from the monitoring device 20 is received by the relay station 37 and relayed by the relay station 37 to the cloud computer server 29. Typically, the relay station 37 is provided with a transceiver for radio communication with the wireless transceiver 30 of the monitoring device 20, and a GSM module for communicating with the cloud computer server 29.

The microprocessor 28 may be programmed as will be described below to transmit the data indicative of the state of the animal 21 at predefined time intervals, and/or in response to an activation signal received by the transceiver 30, transmitted from the relay station 37. It is envisaged that the relay station 37 would transmit activation signals at predefined intervals, for example, of one second to five seconds, which would be received by the transceiver 30 of the monitoring device 20, when the animal 21 to which the monitoring device 20 is attached comes within range of the relay station 37. Alternatively, the microprocessor 28 may be programmed only to transmit the data through the transceiver 30 in response to an activation signal received from one of the relay stations 37 after a predefined time period had elapsed from the previous transmission.

In addition to the transceiver 30, the device 1 also comprises a low energy communications module, which in this embodiment of the invention comprises an NFC module 31, similar to the NFC module 10 of the ear tag of FIGS. 1 and 2. The NFC module 31 is also mounted on the PCB 26 within the housing 22 for communicating in an NFC protocol with an external powered device, which in this embodiment of the invention comprises a smart mobile phone 32. In this embodiment of the invention the NFC module 31 is configured to support two-way communications between the device 20 and the smart phone 32 operating under the control of a software application, namely, an app, which configures the smart phone 32 to communicate in an NFC protocol with the NFC module 31 of the monitoring device 20.

An induction coil 33 formed by an electrically conductive track 34 extending around the periphery 38 of the PCB 26 is configured for powering the NFC module 31 by the smart phone 32 during communication between the NFC module 31 and the smart phone 32. The induction coil 33 is configured to form a loop antenna through which data signals are wirelessly communicated between the NFC module 31 and the smart phone 32 during NFC communication therebetween. The induction coil 33 is electrically coupled to the NFC module 31 and is configured to produce an electrical current for powering the NFC module 31 in response to an electromagnetic field generated by data communication signals transmitted by the smart phone 32 during communications between the NFC module 31 and the smart phone 32.

A battery 35 electrically connected to a pair of electrical contacts (not shown) on the PCB 26 powers the microprocessor 28 and the other components on the PCB 26 which require electrical power. However, the NFC module 31 is not powered by the battery 35 since as discussed above, it is powered by the smart phone 32 during communication through the NFC module 31, thereby saving battery power and extending the life of the battery 35. Although, in certain cases it is envisaged that the NFC module 31 may be powered by the battery 35 during some data transfer operations through the NFC module 31 from the microprocessor 28.

An electronic memory, namely, a memory chip 36 is mounted on the PCB 26 within the housing 22, and is configured to store a unique identifying code of the monitoring device 20, which is unique to that monitoring device. The NFC module 31 is configured to permit reading out of the identifying code from the memory chip 36 in the NFC protocol by the smart phone 32 with the app installed and activated in response to a wake-up signal from the smart phone 32, when the smart phone 32 is brought into close proximity within approximately 50 mm or less of the electronic monitoring device 20. As discussed above with reference to the ear tag 1, on receiving the identifying code of the monitoring device 20, the smart phone 32 is programmed under the app to store the identifying code of the monitoring device 20 cross-referenced with an identifying code of the animal 21, which if not already stored in the smart phone 32 is inputted into the smart phone 32. Relevant data relating to the animal 21 may also be inputted into and stored in the smart phone 32, or may already have been inputted into and stored in the smart phone 32. This data relating to the animal 21 is cross-referenced with the identifying code of the monitoring device 20 stored in the smart phone 32 and is also cross-referenced with the identifying code of the animal. Additionally, or alternatively, the app may configure the smart phone 32 to upload and store the data relating to the animal 21 cross-referenced with the identifying codes of either or both of the monitoring device 20 and the animal 21 to the cloud computer server 29.

Additionally, the app configures the smart phone 32 to programme or to reprogramme the microprocessor 28 of the monitoring device 20 in the NFC protocol through the NFC module 31 of the monitoring device 20 when the smart phone 32 is in close proximity, namely, within 50 mm or less of the monitoring device 20. The microprocessor 28 can be programmed to set the length of the time intervals between the transmission of data through the transceiver 30 of the monitoring device 20. Also the microprocessor 28 can be programmed by the smart phone 32 through the NFC module 31 to set the amount and type of data to be transmitted on each transmission. Furthermore, the microprocessor 28 can be programmed by the smart phone 32 under the control of the app to select the states, conditions and characteristics of the animal to be monitored, and all such programming would be carried out by the smart phone 32 appropriately configured by the app through the NFC module 31. Limits of parameters against which various monitored signals are compared for determining the various states of the animal may be updated in the microprocessor 28 by the smart phone 32 through the NFC module 31.

The state or states, condition, conditions, characteristic or characteristics of the animal may be read from the microprocessor 28 of the monitoring device 20 by the smart phone 32 through the NFC module 31 under the control of the app. Additionally, data may be uploaded to the monitoring device 20 by the smart phone 32 through the NFC module 31 under the control of the app in the smart phone 12.

In this embodiment of the invention the microprocessor 28 is programmed to determine one of the following states of the animal 21, namely, a resting state, feeding, ruminating and a highly active state. The microprocessor 28 continuously samples the signals produced by the accelerometer 27 into a buffer (not shown) at a sampling rate of approximately 12.5 Hz during consecutive first predefined time periods of 10.24 seconds each. At the end of each first predefined time period, the microprocessor 28 computes the average value of the sampled values of the signal read from the accelerometer 27 during that first predefined time period which is indicative of the state of the head 25 of the animal 21, and from this computation determines whether the head 25 of the animal 21 was in a raised state or in a lowered state during that first predefined time period. At the end of each first predefined time period, the microprocessor 28 determines the level of activity of the animal 21 during that first predefined time period from the spread of the sampled values of the signal read from the accelerometer 27 which is indicative of the level of activity of the animal during that first predefined time period.

From the position of the head 25 of the animal 21 and the level of activity of the animal 21, the microprocessor 28 is programmed to determine the state of the animal 21. If the head 25 of the animal 21 is in the lowered state, and the spread of the sampled values of the signal read from the accelerometer 27 indicative of the level of activity of the animal is within a first predefined range of values, the microprocessor 28 determines that the animal 21 is feeding. On the other hand, if the spread of the sampled values of the signal read from the accelerometer 27 which is indicative of the level of activity of the animal is within a relatively low second predefined range of values, which is less than the predefined range of values indicative of feeding, irrespective of the state of the head 25 of the animal 21, the microprocessor 28 determines that the animal is in a resting state. If the head 25 of the animal 21 is determined as being in the raised state, and the spread of the sampled values of the signal read from the accelerometer 27 which is indicative of the level of activity of the animal is within a third predefined range of values which is less than the first predefined range of values and greater than the second predefined range of values, the microprocessor 28 determines that the animal 21 is ruminating.

If the head 25 of the animal 21 is determined as being in the raised state, and the spread of the sampled values of the signal read from the accelerometer 27 which is indicative of the level of activity of the animal is above a predefined value, which is greater than the first predefined range of values indicative of feeding, the microprocessor 28 determines that the animal 21 is in a highly active state.

At the end of each first predefined time period, the microprocessor 28 increments by one an appropriate one of four counters which are configured within the microprocessor 28 and which correspond to the four states of resting, feeding, ruminating and highly active of the animal 21.

At the end of respective consecutive second predefined time periods, which in this embodiment of the invention are of approximately 15 minute durations, the number of first predefined time periods during that second predefined time period during which the animal was in each or any one of the four states of resting, feeding, ruminating and highly active are stored in memory in the microprocessor 28 for subsequent transmission through the transceiver 30 or through the NFC module 31.

In a herd of animals, for example, a herd of cows, each cow will be provided with a monitoring device 20. When supplied to a farmer, the microprocessor 28 will have already been programmed for monitoring the various characteristics and states of an animal, and the various predefined time periods will also have been programmed into the microprocessor 28. However, only the unique identifying code of each monitoring device 20 will be stored in the memory chip 36. No code identifying an animal will have been assigned to any of the monitoring devices 20. Accordingly, as the monitoring devices 20 are being attached to the respective animals 21, the identifying codes of the respective animals must be cross-referenced with the identifying codes of the respective monitoring devices 20 stored in the memory chip 36 of the corresponding monitoring device 20. As discussed above, the identifying codes of each monitoring device 20 and the corresponding animal 1 are stored and cross-referenced in the smart phone 32, although the identifying code of the animal 21 may be written to and stored in the memory chip 36 or the microprocessor 28 of the corresponding monitoring device 20 through the NFC module 31 by the smart phone 32 under the control of the app. As the monitoring devices 5 are being attached to the respective animals 21 the identifying codes stored in the monitoring chips 36 of the respective devices 20 are sequentially read out through the NFC modules of the devices 20 by the smart phone 32. If the identifying code of the corresponding animal 21 has not already been stored in the smart phone 32, the identifying code of the animal 21 corresponding to the monitoring device 20 is entered into the smart phone 32 and cross-referenced with the identifying code of the monitoring device 20 and stored in the smart phone 32 cross-referenced with the identifying code of the monitoring device 20. The stored cross-referenced identifying codes are then uploaded by the smart phone 32 to the cloud computer server 29.

In this embodiment of the invention data indicative of the monitored characteristics and states, and other data relating to the animal is stored in a database of a cloud computer server 29, which supports the monitoring devices 20. Additionally, data which is indicative of the state or states of the animal which is either computed or determined from the data indicative of the characteristics of the animal is stored in the database of the cloud computer server 29. Furthermore, the cloud computer server is programmed to compute and determine the health and other issues of the animal from the monitored data indicative of the monitored characteristics and states of the animal. In this embodiment of the invention the data indicative of the monitored characteristics and states of the animal is transmitted through the transceivers 30 of the monitoring devices 20 to the relay station 37, which in turn uploads the data received from the monitoring devices 20 to the cloud computer server 29 for subsequent processing.

Figure 5:
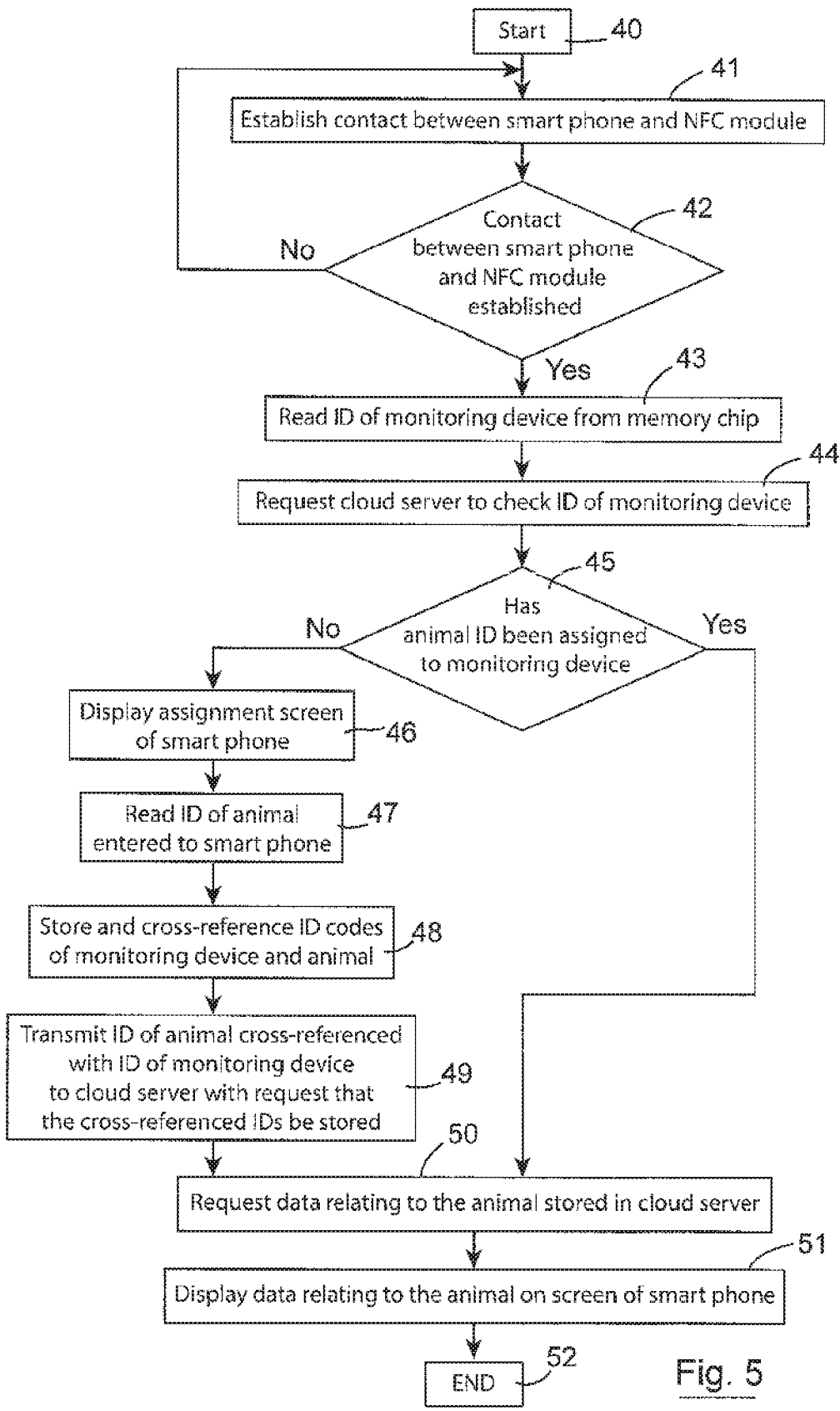
FIG. 5 is a block representation of a routine of a software application with which a smart mobile device is programmed to communicate with the electronic device of FIG. 3.
Figure 6:
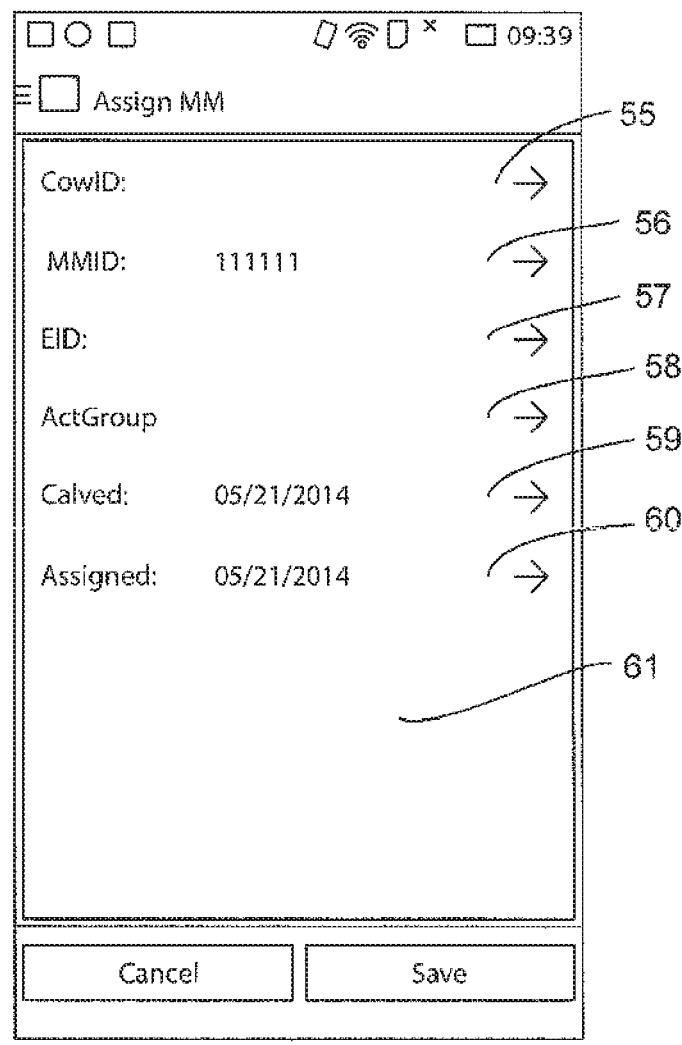
FIG. 6 is a view of a screen of the smart mobile device referred to in FIG. 5 displayed under the control of the software application of FIG. 5.

Referring now to FIGS. 5 and 6, the operation of the smart phone 32 and the monitoring devices 20 under the app for cross-referencing the identification codes of the respective monitoring devices 20 with the identity of the corresponding animals 21 will now be described. FIG. 5 illustrates a routine of the app which is executed by the smart phone 32 under the control of the app each time the smart phone 32 is brought into close proximity with any one of the monitoring devices 20. FIG. 6 illustrates a screen of the smart phone 32 which is configured by the app and presented to a user as the smart phone 32 executes the routine of FIG. 5.

Turning now to FIG. 5, block 40 starts the routine each time the app is called up on the smart phone 32 and the smart phone 32 is brought into close proximity, within 50 mm of any one of the monitoring devices 20 to communicate with the monitoring device 20 in the NFC protocol through the NFC module 31. The routine then moves to block 41, which executes a subroutine in order to establish contact between the smart phone 32 and the monitoring device 20 with which the smart phone 32 is in close proximity in the NFC protocol through the NFC Module 31. On completion of the subroutine of block 41, the routine moves to block 42. Block 42 checks if contact between the smart phone 32 and the NFC module 31 of the monitoring device 20 has been established. If block 42 establishes that contact has not been established between the smart phone 12 and the NFC module 31, the routine returns to block 41. When block 42 determines that contact between the smart phone 32 and the NFC module 31 has been established, the routine moves to block 43. Block 43 calls up a subroutine which causes the smart phone 32 to read the identification code of the monitoring device 20 from the memory chip 36 through the NFC module 31.

On the subroutine of block 43 having read the identifying code of the monitoring device 20 from the memory chip 36, the routine moves to block 44. Block 44 executes a subroutine which establishes contact between the smart phone 32 and the cloud computer server 29 which supports the monitoring devices 20. The identifying code of each monitoring device 20 is pre-stored in the cloud database of the cloud computer server 29 prior to sale of the monitoring devices 20. If this is not the first time that communication has been established with the monitoring device 20 through the NFC module 31 by a smart phone, data relating to the animal to which the monitoring device 20 is attached in general would be stored in the cloud database of the cloud computer server 29, and would be cross-referenced with an identifying code of the animal and would also be cross-referenced with the identifying code of the monitoring device 20 in the cloud computer database of the cloud computer server 29. Once block 44 has established contact between the smart phone 32 and the cloud computer server 29 the routine moves to block 45. Block 45 requests the cloud server to check if an identifying code of an animal has been assigned to the monitoring device 20 and cross-referenced in the cloud computer database of the cloud computer server 29 with the identifying code of the monitoring device 20 which is stored in the cloud computer database.

If block 45 determines that an identifying code of an animal has not been assigned to and cross-referenced with the identifying code of the monitoring device 20 in the cloud computer database, the routine moves to block 46, which displays an assignment screen on the smart phone 32 which allows a farmer to input the identifying code of the animal, to which the monitoring device 20 has just been attached, into the smart phone 32. The assignment screen which is displayed on the smart phone 32 is illustrated in FIG. 6 and is described in more detail below. The identifying code of the animal is displayed on the assignment screen as it is being entered into the smart phone 32. The routine then moves to block 47. Block 47 reads the identifying code of the animal which has been inputted by the farmer into the smart phone 32, and the routine moves to block 48. Block 48 stores the identifying code of the animal cross-referenced with the identifying code of the monitoring device in the smart phone 32, and the routine moves to block 49. Block 49 initiates a subroutine which causes the smart phone 32 to transmit the identifying code of the animal cross-referenced with the identifying code of the monitoring device 20 to the cloud computer server 29, with a request that the cross-referenced identifying codes of the respective monitoring device 20 and the animal 21 to which the monitoring device 20 has been attached be stored in the cloud computer database of the cloud computer server 29.

Under the subroutine of block 49, the smart phone 32 also requests that any data relating to the animal the identifying code of which is cross-referenced with the identifying code of the monitoring device 20 just transmitted to the cloud computer server 29 which is stored in the cloud computer database be cross-referenced with the identifying code of the monitoring device 20 in the cloud computer database. The routine then moves to block 50. Block 50 operates the smart phone 32 to request all data relating to the animal, to which the monitoring device 20 has been attached, which is stored in the cloud server corresponding to the identifying code of the monitoring device 20 be downloaded to the smart phone 32. The routine then moves to block 51. Block 51 displays on the screen of the smart phone 32 the data downloaded from the cloud computer database relating to the animal, the identifying code of which is cross-referenced with the identifying code of the monitoring device 20 in the cloud computer database. On displaying the data relating to the animal on the screen of the smart phone 32, the routine then moves to block 52, which ends the routine.

Returning now to block 45, if block 45 determines that an identifying code of an animal has already been assigned to and cross-referenced with the identifying code of the monitoring device 20 in the cloud computer database, the subroutine moves to block 50, which has already been described, and the routine moves to block 51, which displays the data relating to the animal from the cloud computer database on the assignment screen of the smart phone 32. Typically, if block 45 determined that an animal identifying code had been assigned to and cross-referenced with the identifying code of the monitoring device 20, this would indicate that this was not the first time that the smart phone 32 has been brought into close proximity with the monitoring device 20. Therefore, once the identifying codes of the monitoring device 20 and the animal to which that monitoring device 20 is attached have been stored and cross-referenced in the smart phone, each time the smart phone is brought into close proximity, within 50 mm of that monitoring device 20, and the smart phone 32 executes the app, the identifying code of the animal is displayed on the assignment screen of the smart phone 32, along with any other data of that animal stored in the smart phone 32 or in the cloud computer server database, thereby allowing the farmer to readily identify the animal, and providing the farmer with all stored data relating to the animal.

Referring now to FIG. 6, as mentioned above, FIG. 6 illustrates the assignment screen which is displayed on the smart phone 32 in order to allow a farmer to input the identifying code of an animal to which the monitoring device 20 has been attached into the smart phone 32, and also to display data relating to the animal. The assignment screen of FIG. 6 displays seven fields 55 to 61. The first field 55 is provided for an identifying code of the animal which would be assigned to the animal by a farmer, and as that identifying code of the animal is being entered into the smart phone 32, the identifying code appears in the field 55. Field 56 displays the identifying code which has been read from the memory chip 36 by the smart phone 32. Field 57 allows the national identifying code of the animal which has been assigned to the animal by the State agency to be entered and displayed. Field 58 is provided for the identifying code of the herd of which the animal is a member, or alternatively, a group of animals of the herd, which would be in a similar environment. By knowing to which herd or group of animals from a herd a particular animal belongs, all of which share the same environment as that animal, data relating to that animal received by the cloud computer server 29 can compare the data relating to the state or states of that particular animal with corresponding data from other animals in the same herd or group of animals of which that particular animal belongs, this allows a more accurate determination of the health and other issues of that particular animal to be made by the cloud computer server.

Field 59 is provided for entering the date on which the animal, if, for example, the animal is a cow, the cow calved. Field 60 is provided for entering the date on which the monitoring device 20 has been assigned to an animal. In field 61 other data relating to the animal is displayed, for example, data relating to various states of the animal, the health of the animal and other relevant data relating to the animal which is stored in the cloud database, and downloaded therefrom by the smart phone 32 under block 50 of the routine of FIG. 5.

It will be appreciated that if desired, only one of the identifying codes of the animal may be entered into either field 55 or field 57 of the assignment screen of FIG. 6.

In use, with the monitoring device 20 attached to the neck 24 of the animal 21 by the strap 23 and with the axes of the accelerometer 27 configured to produce a signal indicative of the raised and lowered states of the head 25 of the animal 21 and a signal indicative of the level of activity of the animal 21, the device 20 is ready for use. With the app loaded into the smart phone 32 and activated, the smart phone 32 is brought into close proximity with the monitoring device 20, and the smart phone executes the routine of FIG. 5. When the smart phone 32 is brought into close proximity with the monitoring device 20 for the first time, the farmer inputs the identifying code or codes of the corresponding animal into the smart phone 32, as described with reference to FIG. 5. Each subsequent time that the smart phone 32 is brought into close proximity with the monitoring device 20, data relating to the corresponding animal 21 is downloaded from the cloud database to the smart phone 32 and displayed on the screen thereof as described with reference to FIG. 5.

If it is desired to programme or reprogramme the microprocessor 28 in the monitoring device 20, such programming or reprogramming is carried out by the smart phone 32 through the NFC module 31 with the smart phone 32 operating under the control of the app and in close proximity to the monitoring device 20.

The microprocessor 28 continuously samples the signals produced by the accelerometer 27 at the sampling rate, and at the end of each first predefined time period determines the state of the animal 21 during that first predefined time period. At the end of each second predefined time period, the microprocessor 28 stores the data relating to the states of the animal 21 and the number of the first predefined time periods the animal 21 was in each of those states during that second predefined time period.

On the animal 21 coming within range of the relay station 37, and on receiving an activation signal from the relay station, the microprocessor 28 operates the transceiver 30 to transmit data indicative of the states and the number of times the animal 21 has been in those states for each of the second predefined time periods since such data was last transmitted by the monitoring device 20. The relay station 37 then relays the data to the cloud computer server 29. The cloud computer server 29 determines the health and other states of the corresponding animal 21 by analysing the data received from the monitoring device 20. For example, if the animal is resting excessively, the animal may be in ill health, or lame. If the animal is not feeding sufficiently or not ruminating sufficiently, the animal may be determined as being in ill health. If the animal 21 is in the highly active state for longer periods than animals in the same herd, then the onset of oestrus in the animal may be detected.

Additionally, the microprocessor 28 may be activated by an activation signal from the base station computer to transmit the data indicative of the states of the animal 21 and the number of times the animal 21 has been in those states during each of the second predefined time periods since the last transmission was made by the microprocessor 28 through the transceiver 30, or since the last transmission made by the microprocessor 28 through the transceiver 30 to the relay station 37.

When it is desired to read the stored data relating to the states of the animal and the number of times the animal was in those states during the respective second predefined time periods from the monitoring device 20 through the smart phone 32, the smart phone 32 with the app activated, and in close proximity with the monitoring device 20, is operated to output an activation signal in an NFC protocol to the monitoring device 20. On reception of the activation signal by the NFC module 31, the microprocessor 28 is activated to transmit the data in NFC protocol through the NFC module 31 for reception by the smart phone 32.

Where it is desired to upload data to the monitoring device 20, such data may be uploaded through the NFC module 31 by the smart phone 32 configured to operate under the app and in close proximity to the monitoring device 20.

Where it is desired to identify the animal 21, the smart phone 32 with the app activated is brought into close proximity with the monitoring device 20 to read the identifying code of the monitoring device 20 from the memory chip 36 of the monitoring device 20 so that the identity of the animal 21 can be then readily read from the smart phone 32.

Where it is desired to programme or reprogramme the microprocessor 28 of the monitoring device 20, the smart phone 32 with the app activated is brought into close proximity with the monitoring device 20, and programming or reprogramming of the microprocessor 28 is carried out in an NFC protocol by the smart mobile phone 32 through the NFC module 31 of the monitoring device 20.

While the electronic ear tag and the electronic monitoring device according to the invention have been described as being particular types of devices, the electronic ear tag and the electronic monitoring device may be of any other type, and where the electronic monitoring device is configured to monitor one or more states or one or more characteristics or conditions of an animal, the states, conditions and/or characteristics monitored by the monitoring device may be any states, conditions or characteristics other than those described, for example, the monitoring device may be configured to monitor temperature, heart rate, blood pressure, or any other suitable state or characteristic of the animal. Furthermore, while the electronic monitoring device has been described as comprising an accelerometer for determining the state of the head of the animal and the level of activity of the animal, any other suitable monitoring sensor or sensors may be used. It will also be appreciated that the electronic monitoring device may be attached to the tail of an animal in order to detect the onset of parturition by detecting the state of the tail of the animal, whether the tail is in a raised state or a normal downwardly extending state.

Additionally, it will be appreciated that any other suitable securing means besides a strap may be provided for securing the electronic monitoring device to the animal. It will also be appreciated that other suitable means for attaching the electronic ear tag to the animal besides a stud may be provided. Indeed, in certain cases, it is envisaged that the electronic ear tag, and indeed the electronic monitoring device may be of the type which would be implanted in the animal, but would be located relatively closely to the skin in order to facilitate Near Field Communications with the device.

While a specific sampling rate has been described at which the signals produced by the accelerometer are sampled, any other suitable sampling rates may be used. Needless to say, the first predefined time periods and the second predefined time periods may be of any other suitable or desired duration. In general, the first predefined time period would lie in the range of 5 seconds to 25 seconds, although the first predefined time periods may be of greater or lesser duration. Additionally, the second predefined time periods may lie within a range of from 1 minute to 60 minutes, and indeed in certain cases, the second predefined time periods could be of duration considerably longer than 60 minutes. The duration of the second predefined time periods will largely be set based on the states which are being monitored by the monitoring device.

While the monitoring device has been described as comprising a transceiver and an NFC module, it is envisaged in certain cases that the monitoring device may also be provided with a receiver for receiving identification signals from predefined locations visited by the animal, such as a drinking trough, a feeding trough or the like. The microprocessor would be programmed to read the identification signals and store data relating to the identity of the location visited by the animal, the time of the visit and the duration thereof for subsequent transmission and analysis by the base station computer.

While the signal processor has been described as comprising a microprocessor, any other suitable signal processor may be provided, for example, a microcomputer, a programmable logic controller or any other such signal processor.

It is also envisaged that the transceiver may be operable under the control of the microprocessor in two modes, namely, a high power mode and a low power mode, and would be operated in the high power mode for transmission of data to the relay station 37, when the monitoring device would be out of range of the relay station to receive an activation signal, and would be operated in a low power mode for transmission of data to a relay station when within range of the relay station.

While the electronic devices have been described for monitoring and identifying cows, the electronic devices may be provided for use with any animals.

While the NFC module has been described for communicating with a smart mobile phone, the NFC module may be adapted for communicating wirelessly with any other external powered device, for example, a tablet computer, and such communications would be carried out in an NFC protocol, and would be two way communications.

While the low energy communications module has been described as comprising an NFC module, any other suitable low energy communications module may be provided. For example, the low energy communications module could be provided by a blue tooth low energy communications module.

The invention claimed is:

1. A method for communicating with an electronic memory of an electronic device locatable externally on or internally in an animal, the electronic memory having an identifying code identifying the electronic device stored therein, the method comprising:
    locating a low energy wireless NFC (near field communications) communications module on the electronic device, the low energy wireless NFC communications module being configured to wirelessly communicate with an external powered smart mobile device and with the electronic memory;
    configuring the electronic device to monitor at least one of a plurality of states of the animal and to store data indicative of the monitored state;
    configuring the external powered smart mobile device to wirelessly communicate with the electronic device through the low energy NFC communications module in an NFC protocol, and to wirelessly communicate with a remote computer;
    bringing the external powered smart mobile device into close proximity with the electronic device;
    initiating wireless communication between the external powered smart mobile device and the electronic device through the low energy NFC communications module in the NFC protocol by the external powered smart mobile device;
    wirelessly reading the identifying code identifying the electronic device from the electronic memory of the electronic device by the external powered smart mobile device through the low energy NFC communications module in the NFC protocol;
    entering the identifying code identifying the animal on or in which the electronic device is located into the external powered smart mobile device; and
    storing and cross-referencing the entered identifying code identifying the animal, on or in which the electronic device is located, with the read identifying code identifying the electronic device in the external powered smart mobile device, wherein
    the electronic device comprises a signal processor configured to be wirelessly resettable and programmable by the external powered programmable smart mobile device through the low energy wireless NFC communications module, and a long-range wireless communicating means for communicating the electronic device with a remote computer, and
    the method further comprises:
    permitting wireless resetting of the signal processor by the external powered programmable smart mobile device through the low energy wireless NFC communications module,
    permitting wireless programming of the signal processor by the external powered programmable smart mobile device through the low energy wireless NFC communications module, and
    initiating wireless communication between the long range wireless communicating means with a remote computer through a communicating means configured to communicate with the electronic device and with the remote computer.

2. A method as claimed in claim 1 in which the data indicative of the monitored state of the animal is stored in the external powered smart mobile device cross-referenced with the identifying code of the animal.

3. A method as claimed in claim 1 in which the signal processor of the electronic device is configured to communicate with the external powered smart mobile device through the low energy NFC communications module, and to download data therefrom through the NFC communications module to the external powered smart mobile device.

4. A method as claimed in claim 1 in which the low energy NFC communications module is configured to be electrically powered wirelessly by electromagnetic induction by the external powered smart mobile device.

5. A method as claimed in claim 1 in which the external powered smart mobile device is configured to communicate wirelessly with the remote computer through a telecommunications network.

6. A method as claimed in claim 1 in which data downloaded from the electronic device is uploaded to the remote computer by the external powered smart mobile device.

7. A method as claimed in claim 1 in which the external powered smart mobile device downloads data relating to the animal on or in which the electronic device is located from the remote computer.

8. A method as claimed in claim 1 in which the external powered smart mobile device is programmed by a software application (app) for communicating wirelessly with the electronic device through the low energy NFC communications module.

9. A method as claimed in claim 8 in which the external powered smart mobile device is programmed by the app to display on a visual display screen thereof data downloaded from the electronic device.

10. A method as claimed in claim 8 in which the external powered smart mobile device is programmed by the app to display data relating to the animal on or in which the electronic device is located downloaded from the remote computer in response to the external powered smart mobile device downloading the identifying code of the electronic device from the electronic device.

11. A method as claimed in claim 1 in which the remote computer comprises a cloud computer server.

12. A method as claimed in claim 1 in which the external powered smart mobile device comprises a smart mobile phone.

13. In combination an electronic device configured for locating externally on or internally in an animal, an external powered smart mobile device configured to communicate with the electronic device, the electronic device being configured to monitor at least one of a plurality of states of the animal and to store data indicative of the monitored state, a remote computer, and a communicating means for communicating between the electronic device and the remote computer, the electronic device comprising:
  an electronic memory having an identifying code identifying the electronic device stored therein;
  a low energy wireless NFC communications module located on the electronic device, the low energy wireless NFC communications module being configured to wirelessly communicate with the external powered smart mobile device and with the electronic memory of the electronic device in an NFC protocol,
  a long range wireless communicating means for communicating the electronic device with a remote computer through the communicating means for communicating between the electronic device and the remote computer, and
  a signal processor configured to be wirelessly resettable and programmable by the external powered programmable smart mobile device through the low energy wireless NFC communications module,
the external powered smart mobile device being configured
  to wirelessly communicate with the electronic device through the low energy NFC communications module in the NFC protocol,
  to wirelessly communicate with a remote computer,
  to wirelessly read the identifying code identifying the device stored in the electronic memory of the electronic device through the NFC communications module in the NFC protocol,
  to permit entry of an identifying code identifying the animal on or in which the electronic device is located into the external powered smart mobile device,
  to permit storing and cross-referencing of the identifying code identifying the animal with the identifying code identifying the electronic device in the external powered smart mobile device,
  to permit wireless resetting of the signal processor through the low energy wireless NFC communications module in response to a reset signal received from the external powered programmable smart mobile device, and
  to permit wireless programming of the signal processor through the low energy wireless NFC communications module.

14. The combination as claimed in claim 13 in which the electronic device comprises a monitoring means for monitoring the at least one state of an animal on or in which the electronic device is located, and the signal processor is configured for processing signals read from the monitoring means, and for producing the data indicative of a state of the animal, and to store the data indicative of the state of the animal, and the low energy NFC communications module is configured for wirelessly communicating with the external powered smart mobile device and with the signal processor for downloading the stored data indicative of the state of the animal to the external powered smart mobile device.

15. The combination as claimed in claim 13 in which the low energy NFC communications module is configured to be powered wirelessly by the external powered smart mobile device.

16. The combination as claimed in claim 13 in which the communicating means comprises a relay station comprising a radio transceiver for communicating with the long range wireless communicating means of the electronic device, and a GSM module configured to communicate with the remote computer.

17. A method for communicating with an electronic memory of an electronic device locatable externally on or internally in an animal, the electronic memory having an identifying code identifying the electronic device stored therein, the method comprising:
  locating a low energy wireless NFC (near field communications) communications module on the electronic device, the low energy wireless NFC communications module being configured to wirelessly communicate with an external powered smart mobile device and with the electronic memory,
  configuring the external powered smart mobile device to wirelessly communicate with the electronic device through the low energy NFC communications module in an NFC protocol, and to wirelessly communicate with a remote computer,
  bringing the external powered smart mobile device into close proximity with the electronic device,
  initiating wireless communication between the external powered smart mobile device and the electronic device through the low energy NFC communications module in the NFC protocol by the external powered smart mobile device,
  wirelessly reading the identifying code identifying the electronic device from the electronic memory of the electronic device by the external powered smart mobile device through the low energy NFC communications module in the NFC protocol,
  if an identifying code identifying the animal on or in which the electronic device is attached is not stored and cross-referenced with the read identifying code identifying the electronic device in the external powered smart mobile device, entering the identifying code identifying the animal on or in which the electronic device is located into the external powered smart mobile device, and
  storing and cross-referencing the entered identifying code identifying the animal, on or in which the electronic device is located, with the read identifying code identifying the electronic device in the external powered smart mobile device, wherein the electronic device comprises a signal processor configured to be wirelessly resettable and programmable by the external powered programmable smart mobile device through the low energy wireless NFC communications module, and a long range wireless communicating means for communicating the electronic device with a remote computer, and the method further comprises:

permitting wireless resetting of the signal processor by the external powered programmable smart mobile device through the low energy wireless NFC communications module, permitting wireless programming of the signal processor by the external powered programmable smart mobile device through the low energy wireless NFC communications module, and initiating wireless communication between the long-range wireless communicating means and a remote computer through a communicating means configured to communicate with the electronic device and with the remote computer.

18. In combination an electronic device configured for locating externally on or internally in an animal, and an external powered smart mobile device configured to communicate with the electronic device, the electronic device comprising:

an electronic memory having an identifying code identifying the electronic device stored therein, a low energy wireless NFC communications module located on the electronic device, the low energy wireless NFC communications module being configured to wirelessly communicate with the external powered smart mobile device and with the electronic memory of the electronic device in an NFC protocol, a long range wireless communicating means for communicating the electronic device with a remote computer, through a communicating means for communicating between the electronic device and the remote computer, and a signal processor configured to be wirelessly resettable and programmable by the external powered programmable smart mobile device through the low energy wireless NFC communications module, the external powered smart mobile device being configured to wirelessly communicate with the electronic device through the low energy NFC communications module in the NFC protocol, to wirelessly communicate with a remote computer, to wirelessly read the identifying code identifying the device stored in the electronic memory of the electronic device through the NFC communications module in the NFC protocol, to permit entry of an identifying code identifying the animal on or in which the electronic device is located into the external powered smart mobile device if an identifying code identifying the animal on or in which the electronic device is attached is not stored and cross-referenced with the read identifying code identifying the electronic device in the external powered smart mobile device, to permit storing and cross-referencing of the identifying code identifying the animal with the identifying code identifying the electronic device in the external powered smart mobile device, to permit wireless resetting of the signal processor through the low energy wireless NFC communications module in response to a reset signal received from the external powered programmable smart mobile device, and to permit wireless programming of the signal processor through the low energy wireless NFC communications module.

19. The combination as claimed in claim 18 further comprising the remote computer, and the communicating means for communicating between the electronic device and the remote computer.

20. In combination an electronic device configured for locating externally on or internally in an animal, an external powered smart mobile device configured to communicate with the electronic device, a remote computer, and a communicating means for communicating between the electronic device and the remote computer, the electronic device comprising:

an electronic memory having an identifying code identifying the electronic device stored therein, a low energy wireless NFC communications module located on the electronic device, the low energy wireless NFC communications module being configured to wirelessly communicate with the external powered smart mobile device and with the electronic memory of the electronic device in an NFC protocol, a long-range wireless communicating means for communicating the electronic device with a remote computer, through the communicating means for communicating between the electronic device and the remote computer, and a signal processor configured to be wirelessly resettable and programmable by the external powered programmable smart mobile device through the low energy wireless NFC communications module, the external powered smart mobile device being configured to wirelessly communicate with the electronic device through the low energy NFC communications module in the NFC protocol, to wirelessly communicate with a remote computer, to wirelessly read the identifying code identifying the device stored in the electronic memory of the electronic device through the NFC communications module in the NFC protocol, to permit entry of an identifying code identifying the animal on or in which the electronic device is located into the external powered smart mobile device if an identifying code identifying the animal on or in which the electronic device is attached is not stored and cross-referenced with the read identifying code identifying the electronic device in the external powered smart mobile device, to permit storing and cross-referencing of the identifying code identifying the animal with the identifying code identifying the electronic device in the external powered smart mobile device, to permit wireless resetting of the signal processor through the low energy wireless NFC communications module in response to a reset signal received from the external powered programmable smart mobile device, and to permit wireless programming of the signal processor through the low energy wireless NFC communications module.

* * * * *